United States Patent
Beatty

(10) Patent No.: US 6,734,320 B2
(45) Date of Patent: May 11, 2004

(54) NON-SYMMETRIC, PARTIALLY FLUORINATED LUBRICANT ADDITIVES

(75) Inventor: Richard P. Beatty, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/135,648

(22) Filed: Apr. 30, 2002

(65) Prior Publication Data

US 2002/0173433 A1 Nov. 21, 2002

Related U.S. Application Data

(62) Division of application No. 09/299,251, filed on Apr. 26, 1999, now Pat. No. 6,413,918.
(60) Provisional application No. 60/083,115, filed on Apr. 27, 1998.

(51) Int. Cl.$^7$ ............................................... C07C 69/34
(52) U.S. Cl. .................. 560/87; 560/122; 560/123; 560/124; 560/198
(58) Field of Search .................. 560/87, 122, 123, 560/124, 198; 508/500, 504

(56) References Cited

U.S. PATENT DOCUMENTS 4,016,287 A * 4/1977 Eberhardt et al. .......... 514/617
4,348,399 A * 9/1982 Shepherd ..................... 560/19
4,670,421 A * 6/1987 DeVries et al. ................ 514/63
5,578,387 A * 11/1996 Kai et al. ................. 428/694 T
6,413,918 B1   7/2002 Beatty

FOREIGN PATENT DOCUMENTS

GB       1188186    * 4/1970
JP       2026493    * 12/1968

* cited by examiner

Primary Examiner—Jacqueline V. Howard

(57) ABSTRACT

Novel non-symmetric, partially fluorinated compositions and method of manufacture which are useful as lubricants or as additives to lubricant formulations involving the molecular structure:

$$R_{1f}-F'-R_2-F''-R_{3h}$$

where $R_{1f}$ represents a wholly or partially fluorinated organic residue end group, F' and F" represent functional linkages which may be alike or different, $R_2$ represents the backbone and $R_{3h}$ represents a non-fluorinated organic residue end group. Such compositions are produced by reacting a mixture of alcohols, mercaptans or amines containing at least one partially fluorinated compound and at least one non-fluorinated compound in the mixture, thus producing the $R_{1f}$ and the $R_{3h}$ residues, with a difunctional organic compound (e.g., diacid, dinitrile, disulfonyl halide, diisocyanate, diisothiocyanate, diphosphoryl halide or dithiophosphoryl halide).

1 Claim, 4 Drawing Sheets

NON-SYMMETRIC, PARTIALLY FLUORINATED LUBRICANT ADDITIVES

CROSS-REFERENCE TO RELATED APPLICATIONS

Applicants claim the benefit of Provisional Application 60/083,115 filed Apr. 27, 1998 and Non-Provisional Application 09/299,251 filed Apr. 26, 1999 now allowed.

STATEMENT REGARDING FEDERALLY SPONSORED RESEARCH OR DEVELOPMENT

"Not Applicable"

BACKGROUND OF THE INVENTION

1. Field of the Invention

This invention relates to lubricants. In particular, it describes non-symmetric, partially fluorinated lubricants and additives, which are soluble in lubricating oils and impart anti-wear and friction-reducing benefits to lubricant formulations.

2. Description of the Prior Art

Two of the most important functions of a lubricant are to reduce friction and to reduce wear on moving parts. Full-film lubrication, where moving parts are always separated by a film of lubricant such that the parts never make contact, is an ideal that cannot always be achieved in practice. Design constraints, together with high load, slow speed, lubricant starvation, or low viscosity of the lubricant, may preclude full-film lubrication and increase the severity of contact. These conditions are often unavoidable during normal operation of machinery, and particularly severe during startup and shutdown.

In cases where full-film lubrication cannot be ensured at all times, anti-wear agents and friction modifiers are usually employed to modify the surfaces to be lubricated. Such anti-wear agents modify these surfaces through adsorption or chemical reaction to form a new surface that can reduce friction and resist wear. Many kinds of anti-wear agents are known. Some of the most widely used and relied upon are the zinc dialkyldithiophosphates (ZDDPs), which find application in many different types of lubricants. Although these compounds have been used for many years in passenger car motor oil, their use is currently restricted (0.1% P vs. 0.12% allowed in the previous GF-1 specification) because the phosphorus from ZDDP poisons catalytic converters, leading to increased emissions. It is anticipated that the future use of ZDDP may be reduced even more than the current level. Anti-wear agents, which can be used in place of ZDDP or in addition to it, are therefore of great interest.

Use of fluorinated and partly-fluorinated materials, as lubricants are known. One limitation of the fluorinated and partly-fluorinated materials previously known is their very low solubility in conventional lubricant base fluids such as natural and synthetic hydrocarbons and esters. Although solid additives may be used in lubricants, they pose several problems. For example, it is known that solid polytetrafluoroethylene (PTFE) can be dispersed in lubricant fluids to reduce friction and wear. However, effectiveness of such a dispersed lubricant depends on maintaining the solid PTFE particles in stable dispersion. Achieving an indefinitely stable dispersion is a challenge, particularly in a formulated lubricant, which may contain detergents, dispersants, or surfactants that may destabilize the PTFE dispersion. Particles of a dispersed solid may flocculate over time in use. Such flocculated particle may then plug or restrict flow of the lubricant in the equipment and result in lubricant starvation in critical locations. The use of soluble additives instead of dispersed solid additives eliminates this problem.

Unfortunately, in the case of PTFE, there is no equivalent material that is soluble in common mineral oil base fluid. Other fluorinated materials have been developed as lubricants, including some liquid highly fluorinated materials such as perfluoropolyethers, but even these liquid highly-fluorinated materials are insoluble in common mineral oil base fluids.

Finally, highly fluorinated materials are significantly more expensive than common lubricant base fluids, making it impractical to use highly fluorinated materials themselves as base fluids except in certain specialized uses where lower cost base fluids are not acceptable.

In the prior art, the terms "partly-fluorinated" and "partially fluorinated" can be confusing since they may be used interchangeably, or either one or both terms may used to refer generically to many different types of organic compounds having some but not all of the hydrogen replaced by fluorine substituents. Thus the terms as used in the prior art do not necessarily adequately describe the structure of the molecule in regard to placement of the fluorine substituents.

As used herein the term partly-fluorinated means that both end groups of a molecule are fluorinated to some extent. Partly-fluorinated materials, particularly esters and ethers, have been disclosed as lubricants for magnetic media, for example, Japanese Patent 259482, Japanese Patent 08259501, and U.S. Pat. Nos. 5,578,387; 5,391,814 and 5,510,513.

Japanese Patent 01122026 teaches use of fluorine containing dibasic acid esters derived from diacids up to $C_8$ as lubricants for magnetic media. This publication, as does PCT publication, US/92/08331, teaches that the acid structure from which the diester is formed may have double bonds present. The molecular structures taught by each of these publications may also have fluorine atoms present in each of the end group.

Partly-fluorinated adipic acid diesters, $R_f(CH_2)_xO_2C(CH_2)_4CO_2(CH_2)_xR_f$, have been disclosed as lubricating coatings by Russian patent SU 449925. Bowers et al (*Lubr. Eng.*, July–August, 1956, pages 245–253) studied the boundary lubricating properties of several similar esters. The compounds disclosed in this publication have fluorine present in each of the diester groups that is the fluorination is symmetric. These partly-fluorinated esters have very low solubility in conventional lubricant base fluids and are therefore, of limited utility as additives in such base fluids.

Japanese Patent 2604186 discloses 1,2,3,4-butane-tetracarboxylic acid tetraesters with partly-fluorinated alcohols, but since all four ester groups are derived from fluorinated alcohols, these esters, too, are symmetric. Other examples of the teaching of symmetrically fluorinated molecular structures include U.S. Pat. Nos. 4,203,856; 5,066,856 and 4,039,301 and in JP08258482 and JP08259501.

Fluorine-containing tri-carbonyl compounds, including some esters, are disclosed as lubricant additives in Japanese patent JP 07242584, and partial fluoroesters of polycarboxylic acids, in which the acid functional groups are not completely esterified was taught in U.S. Pat. No. 3,124,533.

BRIEF SUMMARY OF THE INVENTION

In view of the above description of the prior art, it is an object of the present invention to provide a fluorinated lubricant additive which can serve as an anti-wear agent and friction reducer that is compatible with conventional lubricant base fluids and which overcomes the cost and solubility limitations of highly fluorinated solid and liquid materials. This object has been achieved in non-symmetric, partially fluorinated compositions and compounds of the present invention.

Thus, the present invention provides a composition for use as a lubricant or an additive to a lubricant formulation comprising an organic molecular structure wherein said structure is a non-symmetric, partially fluorinated structure having backbone formed from alkyl groups, aromatic groups or mixtures of alkyl and aromatic groups, at least two functional linkages joining end groups to the backbone and end groups, wherein at least one end group is wholly or partially fluorinated and at least one other end group contains only atoms selected from the group consisting of hydrogen, carbon, nitrogen, oxygen, sulfur, phosphorous and chlorine.

The functional linkages of the present invention contain atoms selected from the group consisting of oxygen, nitrogen, sulfur, and phosphorous. Preferred functional linkages include carboxylic esters, thioesters, sulfonic esters, ureas, thioureas, amides, phosphates, thiophosphates, imines, amines, ethers, thioethers, urethanes, thiourethanes, sulfoxides, and sulfones.

The present invention also provides a process for synthesizing the present composition comprising the steps of:

a) forming a reaction mixture containing components A and B which when reacted form functional linkages wherein A is a mixture of two or more compounds containing at least one reactive functional group selected either from the group consisting of alcohol, mercaptan and amine or from the group consisting of carboxylic acid, acid anhydride, acid chloride, carboxylic ester, nitrile, sulfonyl halide, isocyanate, isothiocyanate, aldehyde, ketone, alkyl halide, phosphoryl halide, thiophosphoryl halide, phosphoric anhydride, and thiophosphoryl anhydride, and further wherein at least one of said compounds of said mixture is a partially fluorinated compound and at least one other of said compound of said mixture is a non-fluorinated compound; and wherein B is a compound containing at least two reactive functional groups which are the same or different and are capable of reacting with the reactive functional groups present in A and said reactive functional groups of B are selected either from the group consisting of alcohol, mercaptan and amine or from the group consisting of carboxylic acid, acid anhydride, acid chloride, carboxylic ester, nitrile, sulfonyl halide, isocyanate, isothiocyanate, aldehyde, ketone, alkyl halide, phosphoryl halide, thiophosphoryl halide, phosphoric anhydride, and thiophosphoryl anhydride; with the proviso: (i) that when the functional groups of either A or B are alcohols, then the functional groups of B or A, respectively, are selected from the group consisting of (ii) that when the functional groups of either A or B are mercaptans, then the functional groups of B or A, respectively, are selected from the group consisting of acid halide, isocyanate and alkyl halide; and (iii) that when the functional groups of either A or B are amines, then the functional groups of B or A, respectively, are selected from the group consisting of carboxylic acid, acid anhydride, acid chloride, carboxylic ester, isocyanate, aldehyde and ketone; and b. reacting the mixture to form the functional linkages, and c. recovering a non-symmetric, partially fluorinated composition having a molecular structure:

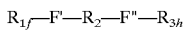

Where: $R_{1f}$ represents a wholly or partially fluorinated $C_1$ to $C_{40}$ organic residue end group; F' and F'' represent functional linkages which are either alike or different and are selected from the group consisting of carboxylic esters, thioesters, sulfonic esters, ureas, thioureas, amides, phosphates, thiophosphates, imines, amines, ethers, thioethers, urethanes, thiourethanes, sulfoxides, sulfones, and mixtures thereof; $R_2$ represents the hydrocarbon backbone selected from the group consisting of a $C_1$ to $C_{30}$ alkyl, cycloalkyl, and aromatic group and mixtures thereof; and $R_{3h}$ represents a non-fluorinated $C_1$ to $C_{40}$ organic residue end group.

The preferred structures for component A useful in the present invention include the following, where X represents an —OH, —SH, —NH$_2$ or —NHR' group:

$F(CF_2)_xCH_2X$; $H(CF_2)_xCH_2X$, wherein x is 1 to about 20; mixtures of the telomers of $F(CF_2CF_2)_xCH_2CH_2X$, wherein x is 1 to about 10 and preferably having an average x of from about 3.5 to about 3.9; mixtures of the telomers of $F(CF_2CF_2)_x(CH_2CH_2O)_yH$, wherein x is 1 to about 10 and y is 1 to 20 and preferably having an average x of about 3.9 and an average y of about 8, and of the telomers of $F(CF(CF_3)CF_2O)_xCF(CF_3)CH_2X$, wherein x is 1 to about 12 and preferably having an average x of about 6.7.

The preferred structures for component B useful in the present invention include the difunctional carboxylic acid, acid anhydride, acid chloride, carboxylic ester, nitrile, sulfonyl halide, isocyanate, isothiocyanate, aldehyde, ketone, alkyl halide, phosphoryl halide, thiophosphoryl halide, phosphoric anhydride, and thiophosphoryl anhydride.

Diacids useful in the present invention include those having from about 4 to 24 carbons, the corresponding acid anhydrides and dimer acids having up to 36 carbons. Acid halides, sulfonyl halides, isocyanates, isothiocyanates, phosphoryl halides and thiophosphoryl halides having structures corresponding to these diacids are also useful in the present invention. Although the preferred structures of the compounds of the present invention are the structures having like functional groups, structures may have mixed functional groups, for example, carboxylic acid/sufonyl halide, carbonyl/carboxylic acid or other combinations.

The present invention includes a lubricant composition comprising a base fluid mixed with the non-symmetric, partially fluorinated compounds of the present invention.

DETAILED DESCRIPTION OF THE INVENTION

Figure 1:
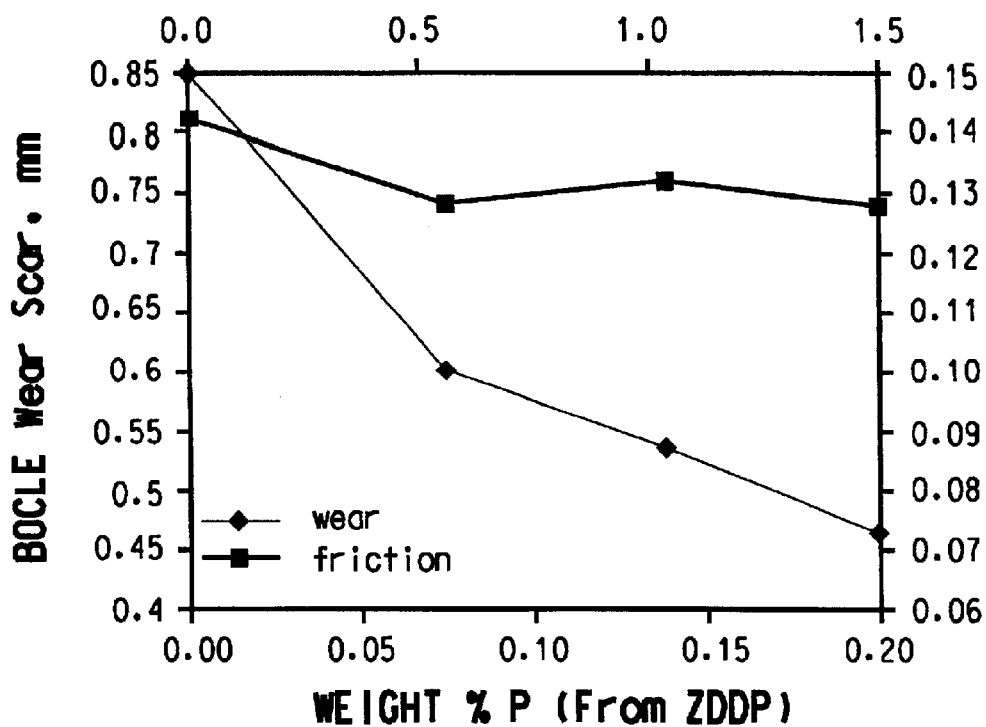
FIG. 1 shows friction and wear performance of ZDDP in 150N oil, for the purpose of comparison with the reduction in friction and wear observed with compositions and compounds of the present invention.

The present invention provides a composition for use as a lubricant or an additive to a lubricant formulation comprising an organic molecular structure wherein said structure is a non-symmetric, partially fluorinated structure having backbone formed from alkyl groups, aromatic groups or mixtures of alkyl and aromatic groups, at least two functional linkages joining end groups to the backbone and end groups, wherein one end group is wholly or partially fluorinated and the other end groups contain only atoms selected from the group consisting of hydrogen, carbon, nitrogen, oxygen, sulfur, phosphorous and chlorine. For example, a molecular structure of the present invention may be illustrated as follows:

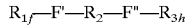

where $R_{1f}$ represents a wholly or partially fluorinated organic residue end group, F' and F" represent functional linkages which may be alike or different, $R_2$ represents the backbone and $R_{3h}$ represents a non-fluorinated organic residue end group. The compounds corresponding to this molecular structure are defined for purposes of this invention as being non-symmetric, partially fluorinated structures.

The functional linkages of the present invention contain atoms selected from the group consisting of oxygen, nitrogen, sulfur, and phosphorous. Preferred functional linkages include carboxylic esters, thioesters, sulfonic esters, ureas, thioureas, amides, phosphates, thiophosphates, imines, amines, ethers, thioethers, urethanes, thiourethanes, sulfoxides, and sulfones.

The preferred structures of the present invention include compounds where F and F' is the same linkage. $R_{1f}$ and $R_{3h}$ may be, but need not be alike.

By non-symmetric, partially fluorinated structure is meant an organic compound having some of the hydrogen replaced by fluorine and having the fluorine concentrated in one region of the structure. For example, the following is a structure for a diester according to the present invention, $R_f(CH_2)_xO_2C$—R—$CO_2R_h$, where $R_f$ is a partly or completely fluorinated group, $R_h$ is a non-fluorinated group, and $x \geq 1$. Such diesters synthesized according to the process of the present invention may also contain non-fluorinated diesters, $R_hO_2C$—R—$CO_2R_h$, and symmetrically-fluorinated diesters, $R_f(CH_2)_xO_2C$—R—$CO_2(CH_2)_xR_f$ byproducts. In terms of structural components, $R_f$ and $R_h$ are end groups —R— is the backbone and —$O_2C$— is the functional linkage. The preferred backbone is formed from a hydrocarbon chain which may be alkyl, aromatic, or a mixture of alkyl (branched, cyclic or straight chains) and aromatic units. It is preferred that unsaturation such as alkylene groups in the backbone be avoided if the additive is to be stable under conditions of use. It should be further appreciated that the backbone can optionally contain more than two functional groups and as such other B molecules such as neopentyl glycol, trimethylolproprane, pentaerythritol, and the like are contemplated as being useful in the present invention.

The term base fluid means a lubricating material, liquid or solid used as the major component in a lubricant formulation. Base fluids are combined with other substances to make fully formulated lubricants for use in reducing friction and wear. A base fluid may be synthetic or natural.

The non-symmetric, partially fluorinated compounds of the present invention may be derived, for example in the case of an ester, from a diacid, at least one partially fluorinated alcohol, $R_fOH$, and at least one non-fluorinated alcohol, $R_hOH$, or their functional equivalents. In this shorthand, $R_f$ represents a partially or wholly fluorinated group and $R_h$ represents a non-fluorinated group. The functional linkage is the —COO— group forming the ester. The diester according to the present invention is a mixture of at least 3 generic components: $R_fO(O)C$—$(CH_2)_x$—$C(O)OR_f$, $R_hO(O)C$—$(CH_2)_x$—$C(O)OR_h$, and $R_hO(O)C$—$(CH_2)_x$—$C(O)OR_f$. Since in commercially available compounds $R_fOH$ and $R_hOH$ are themselves generally mixtures, the diester products are even more complicated mixtures containing all possible combinations of $R_f$ and $R_h$. That is, each of the three generic components is itself a mixture. $R_f$ is derived from the partly-fluorinated alcohol, $R_h$ from the non-fluorinated alcohol, and the central part of the diester, —$O(O)C$—$(CH_2)_x$—$C(O)O$— can be thought of as derived from a diacid, $HO(O)C$—$(CH_2)_x$—$C(O)OH$.

The diester simply serves as an example of one of the many compounds of the present invention. Other functional linkages may be formed in the same fashion as the ester functional linkage by proper selection of the reaction components. For example, one component may be represented by "A" and the other by "B". The functional linkages are formed in the reaction of A with B. In all cases A represents a mixture of the class or classes of compounds that are to be reacted with B; and A is a mixture of two or more compounds wherein at least one of these compounds is a partially fluorinated compound and the other compounds are non-fluorinated compounds; with the proviso that when A is a mixture of alcohols, B is an selected from the group consisting of diacids and diacid equivalents, nitrites, sulfonyl halides, isocyanates, isothiocyanates, phosphoryl halides and thiophosphoryl halides; when A is a mixture of mercaptans, B is selected from the group comprising carboxylic acid halides, isocyanates and alkyl halides; and when A is a mixture of amines, B selected from the group consisting of carboxylic acids and acid equivalents, isocyanates, aldehydes and ketones.

Again for illustration considering the reaction of a mixture of alcohols (A) with a diacid or mixture of diacids (B), theoretically when an alcohol mixture that is 50 mole percent non-fluorinated alcohol and 50 mole percent fluorinated alcohol, the mole percent composition of the mixed diester product is 50 mole percent non-symmetric, partially fluorinated diester, and 25 mole percent each symmetrically fluorinated diester and hydrocarbon diester. As the composition of the alcohol mixture is changed with respect to the ratio of fluorinated to non-fluorinated alcohol, the composition of the ester mixture resulting from the reaction changes according to the probability of producing diesters of symmetric and non-symmetric structures. The inventor has found that the presence of the non-symmetric, partially fluorinated diester in the mixed ester product of amounts as low as 1 mole percent produces dramatic reduction in friction when the mixture is used alone or formulated into a base fluid. That is to say that a mixture containing 1 mole percent of the compound of the present invention, present in a lubricant equal to about 0.2% fluorine content in the overall lubricant formulation, results in a dramatic reduction in friction and wear. Also any composition of a resulting diester mixture, or other mixtures of the present invention, may be adjusted to reduce the amount symmetric, fluorinated diester present by dewaxing the composition, as is illustrated in the Examples below. End groups, backbones and function linkages of the present invention may be selected according to the listing below. This listing is not exhaustive, but lists examples of functional linkages which provide ligands for metal surfaces. For example, metal compositions present at typical steel surfaces might comprise iron and various iron oxides as well as other metals and oxides from other metallic components present in the steel alloy (most commonly other first-row transition metals, notably Cr and Ni, though second-row and third-row metals may also be present). Effective ligands for such metal compositions include organic compounds containing atoms with unshared electron pairs which can serve as Lewis base electron-pair donor ligands to form donor-acceptor bonds with metal compositions. Thus, suitable functional linkages include any functional linkage that forms an effective ligand with the surface of the substrate that is to be lubricated. In a sense the structures of the present invention may be thought of as a combination of a high lubricity fluorinated end, a functional linkage that both connects the end to the backbone of the structure and forms a ligand-like association with the surface to be lubricated and a hydrocarbon tail which provides solubility in the base fluid.

Selection of Structural Components

| Functional Group 1 | Functional Group 2 | F Linkage |
|---|---|---|
| Alcohol | Carboxylic acid, acid anhydrides, carboxylic esters, nitrile, or carboxylic acid halide (e.g. chloride) | Carboxylic ester |
| Mercaptan | Carboxylic acid halide (e.g. chloride) | Thioester |
| Alcohol | Sulfonyl halide (e.g. $RSO_2Cl$) | Sulfonic ester |
| Alcohol | Isocyanate | Carbamates (Urethanes) |
| Alcohol | Isothiocyanate | Thiourethane |
| Amine | Isocyanate | Urea |
| Mercaptan | Isocyanate | Thiourea |
| Amine | Carboxylic acid, Carboxylic acid halide or ester | Amide |
| Alcohol | Phosphoryl halide (e.g. chloride) | Phosphate (O donor atoms) |
| Alcohol | Thiophosphoryl halide (e.g. chloride) | Thiophosphate (S or O donor atoms) |
| Amine | Carbonyl compound (aldehyde or ketone) | Imine, amine (after reduction) |
| Alcohol | Alkyl halide | Ether |
| Mercaptan | Alkyl halide | Sulfide (Thioether) |
| Alcohol | Phosphoric anhydride | Dialkylphosphoric acid ester |

-continued

| Functional Group 1 | Functional Group 2 | F Linkage |
|---|---|---|
| Alcohol | Thiophosporic anhydride | Dialkyl dithiophosporic acid ester |
|  | Oxidation of sulfides (see above) | Sulfoxides and Sulfones |

The previously known, symmetrical, highly-fluorinated compounds, for example, diesters, $R_fO(O)C-(CH_2)_x-C(O)OR_f$, have low solubility in the mineral oils commonly used as lubricant base fluids and poor low-temperature properties, which limits their use as lube additives. It is the mixed, non-symmetric, partially fluorinated diesters, $R_hO(O)C-(CH_2)_x-C(O)OR_f$, which is the main object of this invention. However, it is generally not necessary to separate the desired non-symmetric, partially fluorinated diesters from the highly fluorinated and non-fluorinated diesters products also present in the reaction mixture.

Although usually not necessary, if desired, the mixed products of the present invention may be purified by centrifugation, distillation, fractional crystallization, filtration, extraction, or other standard methods known to those skilled in the art.

Preparation of the compositions of the present invention may be achieved, for example by 1) preparing the compounds of the invention using a limited, less than stoichiometric, amount of fluorinated component in the synthesis and 2) preparing the compounds of the present invention from a mixture of at least one fluorinated "A" compound and one non-fluorinated "A" compound, preferably a mixed-isomer, long-chain, non-fluorinated component of class "A".

The process of the present invention comprises the steps of:

a) forming a reaction mixture containing components A and B which when reacted form functional linkages wherein A is a mixture of two or more compounds containing at least one reactive functional group selected either from the group consisting of alcohol, mercaptan and amine or from the group consisting of carboxylic acid, acid anhydride, acid chloride, carboxylic ester, nitrile, sulfonyl halide, isocyanate, isothiocyanate, aldehyde, ketone, alkyl halide, phosphoryl halide, thiophosphoryl halide, phosphoric anhydride, and thiophosphoryl anhydride, and further wherein at least one of said compounds of said mixture is a partially fluorinated compound and at least one other of said compound of said mixture is a non-fluorinated compound; and wherein B is a compound containing at least two reactive functional groups which are the same or different and are capable of reacting with the reactive functional groups present in A and said reactive functional groups of B are selected either from the group consisting of alcohol, mercaptan and amine or from the group consisting of carboxylic acid, acid anhydride, acid chloride, carboxylic ester, nitrile, sulfonyl halide, isocyanate, isothiocyanate, aldehyde, ketone, alkyl halide, phosphoryl halide, thiophosphoryl halide, phosphoric anhydride, and thiophosphoryl anhydride; with the proviso: (i) that when the functional groups of either A or B are alcohols, then the functional groups of B or A, respectively, are selected from the group consisting of carboxylic acid, acid anhydride, acid chloride, carboxylic ester, acid anhydride, nitrile, sulfonyl halide, isocyanate, isothiocyanate, phosphoryl halide, thiophosphoryl halide and alkyl halide; (ii) that when the functional groups of either A or B are mercaptans, then the functional groups of B or A, respectively, are selected from the group consisting of acid halide, isocyanate and alkyl halide; and (iii) that when the functional groups of either A or B are amines, then the functional groups of B or A, respectively, are selected from the group consisting of carboxylic acid, acid anhydride, acid chloride, carboxylic ester, isocyanate, aldehyde and ketone; and d. reacting the mixture to form the functional linkages, and e. recovering a non-symmetric, partially fluorinated composition having a molecular structure:

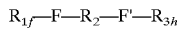

Where: $R_{1f}$ represents a wholly or partially fluorinated $C_1$ to $C_{40}$ organic residue end group; F and F' represent functional linkages which are either alike or different and are selected from the group consisting of carboxylic esters, thioesters, sulfonic esters, ureas, thioureas, amides, phosphates, thiophosphates, imines, amines, ethers, thioethers, urethanes, thiourethanes, sulfoxides, sulfones, and mixtures thereof; $R_2$ represents the hydrocarbon backbone selected from the group consisting of a $C_1$ to $C_{30}$ alkyl, cycloalkyl, and aromatic group and mixtures thereof; and $R_{3h}$ represents a non-fluorinated $C_1$ to $C_{40}$ organic residue end group.

The reaction used to form the functional linkage from components A and B may be any of the methods known in the art. In some cases particular reaction methods may be more favorable because of rate, and or the ability to remove unwanted byproducts such as water.

As the fluorinated component of the mixture "A", alcohols may be more easily found since there are several types commercially available. Examples of common partly-fluorinated alcohols useful in the present invention include 1H, 1H, 2H, 2H-perfluoroalkanols, where $F(CF_2CF_2)_x CH_2CH_2OH$, are preferred, with mixtures where x is at least 1; $F(CF_2)_x CH_2OH$ alcohols, for example, 1H, 1H-heptafluoro-1-butanol; and 1H, 1H-perfluoro-1-octanol; $H(CF_2)_x CH_2OH$ alcohols, for example, 1H, 1H, 5H-octafluoro-1-pentanol; $F(CF_2CF_2)_x CH_2CH_2OH$ alcohols, for example, 1H, 1H, 2H, 2H-perfluoro-1-octanol mixtures with average x of about 3.5 or about 3.9 (referred to as Telomer alcohol-L and Telomer alcohol respectively); $F(CF_2CF_2)_x(CH_2CH_2O)_yH$, generally mixtures with average x of about 3.9 and y about 8, for example, Telomer ethoxylate alcohol; and $F(CF(CF_3)CF_2O)_x CF(CF_3)CH_2OH$, generally mixtures with average x of about 6.7, for example, poly HFPO alcohol. In the present process one may also use as components of the mixture "A", mercaptans or amines having structures similar to or derived from the available alcohols; for example, $F(CF_2CF_2)_x CH_2CH_2SH$ and $F(CF_2CF_2)_x CH_2CH_2CH_2NH_2$.

Virtually any non-fluorinated compound of class "A" may be used to prepare the non-symmetric, partially fluorinated compounds of the present invention. The non-fluorinated alcohols preferred for this invention are those commonly used in lubricant ester fluids, typically higher aliphatic alcohols such as those described in Kirk Othmer, Volume 1 (1991). These include mixtures, such as Exxal 13, tridecyl alcohol, manufactured by Exxon, indicated on the Material Safety Data Sheet to be "Alcohols, C11–C14, iso." Such alcohols produce esters with desirable physical properties to be used as lubricants and lubricant additives.

In the cases where amines or mercaptans serve as the non-fluorinated component of mixture "A", one may use any suitable amines or mercaptans. Those having structures corresponding to or derived from the available alcohols described in the paragraph immediately above are preferred.

The preferred diacids for the present invention are those diacids commonly used in forming lubricant ester fluids. These are most commonly straight chain diacids, $HO(O)C—(CR_2)_x—C(O)OH$, wherein each R is independently selected from H or $C_1$ to $C_4$ alkyl group. Most commonly, all R=H and x=1 to about 12. The most available and widely used diacids are adipic, azelaic, sebacic, and dodecanedioic acids, which contain 6, 9, 10, and 12 carbons respectively. However branched structures such as 2-methylglurtaric acid are acceptable. Also, two or more R may be conjoined to form cyclic structures such as in $C_{36}$ "dimer acid." Mixtures of diacids may be used, such as $C_{36}$ "dimer acid" or CORFREE® M1, from Dupont, which is a mixture of mainly $C_{10}$-$C_{12}$ diacids. Preferred diacids include adipic, 2-methylglutaric, 2-ethylsuccinic, CORFREE M1 and longer chain acids such as Dodecanedioic acid (DDDA). Selection of diacid and other "B" group chain lengths will depend on the lubricant application for which the additive is to be used. In liquid lubricant formulations the "B" group chain length, in combination with the non-fluorinated "A" group is selected so that the additive is soluble in the liquid base fluid. For solid lubricants, the chain lengths can be such that the additive is either a liquid or solid, which is soluble or compatible with the base fluid. It may even be desirable to use a composition of the present invention alone as a lubricant.

It should be further appreciated that either A or B or both may be optionally substituted with functional groups which do not interfere in the reaction of A with B to form the desired functional linkages. For example, the respective components may contain ether linkages, such as in ethoxylated or propoxylated amines or alcohols, or ether amines such as $ROCH_2CH_2CH_2NH_2$. They may also contain linear, branched or cyclic arrangements of atoms and may contain more than one branched groups that may be the same or different.

TEST METHODS

Samples were tested using the ball-on-cylinder (BOCLE) test, described in ASTM D5001. Wear was quantified by the size of the wear scar on the ball, measured at the end of the test. A smaller wear scar indicated less wear. The coefficient of friction was calculated from the ratio of the tangential (lateral) force on the ball to the downward (normal) force on the ball. In all cases, the normal force was 12,00 grams (see Table 1). Several modifications were made to the test, as summarized in Table 1. These changes are expected to make the test a more severe test of anti-wear and friction modifying properties, as described below.

TABLE 1

Ball-on-cylinder test conditions.

| Standard ASTM D5001 | Modified D5001 (consequence) |
|---|---|
| 0.5" ball | 0.25" ball (smaller contact area) |
| 25° C. | 80° C. (lower lubricant viscosity) |
| 1000 g load, 30 minutes | 500 g break in load, 0.5 minute, followed by 6000 g test load, 30 minutes (higher contact pressure; note that a 6000 g load produces a 12,000 g normal force at the ball-cylinder contact point) |
| No friction data | Calibrated load cell to measure tangential force on ball during test (allows calculation of coefficient of friction from ratio of tangential force to normal force, 12,000 g) |

The relative performance of the materials of the present invention was evaluated as additives in a mineral oil base fluid. A commonly available high-quality solvent-refined 150 neutral oil (150N) available from Conoco (about ISO 32 viscosity grade) was selected as the mineral oil base fluid. A grade of oil such as 150N might be used as one component for blending of an oil for use in an internal combustion engine. 150N contains no additives. This 150N oil was tested according to the modified BOCLE method numerous times, the average of these results is summarized in Table 2.

TABLE 2

Solvent refined 150N oil BOCLE results

| Solvent-refined 150N oil | Coefficient of friction | Wear scar, mm |
|---|---|---|
| Number of measurements | 9 | 13 |
| Average | 0.1424 | 0.851 |
| Standard deviation | 0.0052 | 0.042 |
| 95% Confidence interval | ±0.00399 | ±0.025 |

For comparative purposes, the friction and wear performance of several fully formulated (ILSAC GF-1), commercially available passenger car motor oils were measured. The oils tested included two leading full synthetics (MOBIL 1 5W30, Castrol SYNTEC 5W50) and one conventional non-synthetic oil (MOTORCRAFT 5W30). Performance of all three oils was very similar, as summarized in Table 3. This may be because all three contain similar amounts of zinc dialkyldithiophosphate (ZDDP), an extremely effective anti-wear agent. The effect of varying concentration of ZDDP ("Elco 106" purchased from Ideas, Inc.) is shown in FIG. 1. The data in this Figure serves as to provide a standard for comparison of the improvement in lubrication achieved by mixing a hydrocarbon lubricant with the non-symmetric partially fluorinated compositions of the present invention.

TABLE 3

Commercially Available GF-1 Motor Oil BOCLE Test Results

| Formulated GF-1 Motor oils | Coefficient of friction | Wear scar, mm |
|---|---|---|
| Number of measurements | 2 | 9 |
| Average | 0.1313 | 0.499 |
| Standard deviation | 0.0029 | 0.029 |
| 95% Confidence interval | ±0.0260 | ±0.022 |

To determine the efficacy of the additives made according to the present invention, their effect on friction and wear was measured as a function of their concentration in the standard 150N oil. Note that there are two approaches to obtaining a given level of fluorine in a blended lubricant. An additive containing a high level of fluorine can be used at a low treat rate or an additive containing a low level of fluorine can be used at a high treat rate. These two approaches do not necessarily give the same performance.

The following Examples illustrate the present invention, but are not intended to be limiting.

EXAMPLE 1

The following Example describes the condensation esterification of DDDA using Fascat 2003 catalyst, a tin-based esterification catalyst from Elf Atochem, and the preparation of DDDA diesters with varying mole percent Telomer alcohol and Exxal 13.

Reaction mixtures were prepared in 20 mL vials with the compositions indicated in table 4 below. One drop of Fascat 2003 (a product of Atochem) was added to each vial, and the reactions were heated at 200–250° C. for about 12 hours under a nitrogen sweep to remove evolved water. GC analysis of the reaction mixtures showed the expected three component ester mixture: $R_fO(O)C-(CH_2)_x-C(O)OR_f$; $R_hO(O)C-(CH_2)_x-C(O)OR_h$; and $R_hO(O)C-(CH_2)_x-C(O)OR_f$. The actual amount of each ester component present varied as expected with the relative amounts of Telomer alcohol and Exxal 13 present in the synthesis mixture. The appearance of the mixture formed from the respective additive and 150N oil as well as the solubility of the additive in 150N oil are also summarized in the Table 4. It is noteworthy that the fully fluorinated diester, vial 8, was more soluble when heated, but that the solution cooled to a gel-like state as the diester reprecipitated with cooling. Such behavior is very undesirable in a lubricant. This illustrates an important deficiency of the fully fluorinated diesters, since lubricants are often subjected to temperature cycling, and low-temperature performance is often critical.

TABLE 4

DDDA diesters with Telomer alcohol and Exxal 13

| No. | DDDA (mmol) | Telomer alcohol (mmol) | Exxal 13 (mmol) | mol % Telomer alcohol vs total alcohol | Appearance | Solubility in 150 N oil at 25° C. |
|---|---|---|---|---|---|---|
| 1 | 5.15 | 0.29 | 10.74 | 3 | liquid | ≧20% |
| 2 | 4.94 | 0.58 | 10.51 | 5 | liquid |  |
| 3 | 5.15 | 1.34 | 9.88 | 12 | honey-like | >1% |
| 4 | 5.05 | 2.4 | 8.81 | 21 | very thick oil |  |
| 5 | 5.05 | 4.4 | 6.62 | 40 | grease like | ≦0.5% |
| 6 | 5.13 | 5.62 | 5.47 | 51 | grease like | ≈0.25% |
| 7 | 5.15 | 8.26 | 2.78 | 75 | beeswax like |  |
| 8 | 5.34 | 11.06 | 0 | 100 | paraffin like | ≦0.1% |

Figure 2:
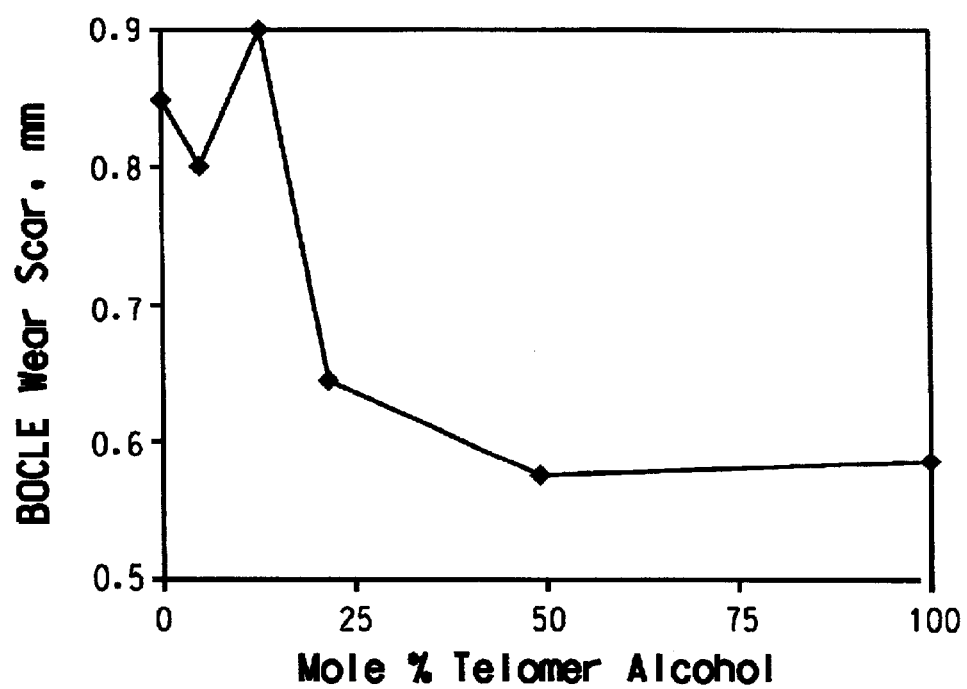
FIG. 2 shows BOCLE wear as a function of the mole percent of the fluorinated telomer alcohol in the mixed alcohol reactant of Example 1.

Wear test results for some of the above materials are shown in FIG. 2. It is clear from this figure that most of the wear benefit is achieved with only about 20 mole % Telomer alcohol in the diester. The wear response, quite surprisingly, is extremely non-linear. This is contrary to the linear response that might be expected if the wear-reducing effects were simply the net average from the concentration present of completely fluorinated diester (100% Telomer alcohol) and non-fluorinated ester (0% Telomer alcohol). This implies that the non-symmetric, partially fluorinated diesters of the present invention have better wear reducing properties than either the non-fluorinated or completely fluorinated diesters.

EXAMPLE 2

The following Example describes the condensation esterification of DDDA using p-toluenesulfonic acid catalyst and the preparation of DDDA diester using a mixture of 50 mole % Telomer alcohol and 50 mole % Exxal 13 followed by a "dewaxing" hexane extraction to remove the symmetrically fluorinated component from the mixed ester product.

A mixture of 230.3 g DDDA (1.0 mole), 474.64 g Telomer alcohol (1.05 mole), 207.91 g Exxal 13 (1.05 mole), and 1.9 g p-toluenesulfonic acid (0.01 mole) were charged to a reactor fitted with a Dean-Stark trap and condenser. The Dean-Stark trap was filled with additional Exxal 13. The reaction was heated and sparged with nitrogen to remove water. The nitrogen sparge was removed and the reaction heated to 280° C. under vacuum (≦0.07 kPa). A portion of the crude ester (610 g) was stirred with 1700 g hexane. The hexane solution was decanted and filtered from undissolved, highly fluorinated material. The hexane solution was treated with activated charcoal and filtered, then with basic alumina and filtered again. Hexane was removed by distillation. Elemental analysis of the residue showed 29.56% F, in good agreement with 28.3% F by $^1$H NMR analysis.

Figure 3:
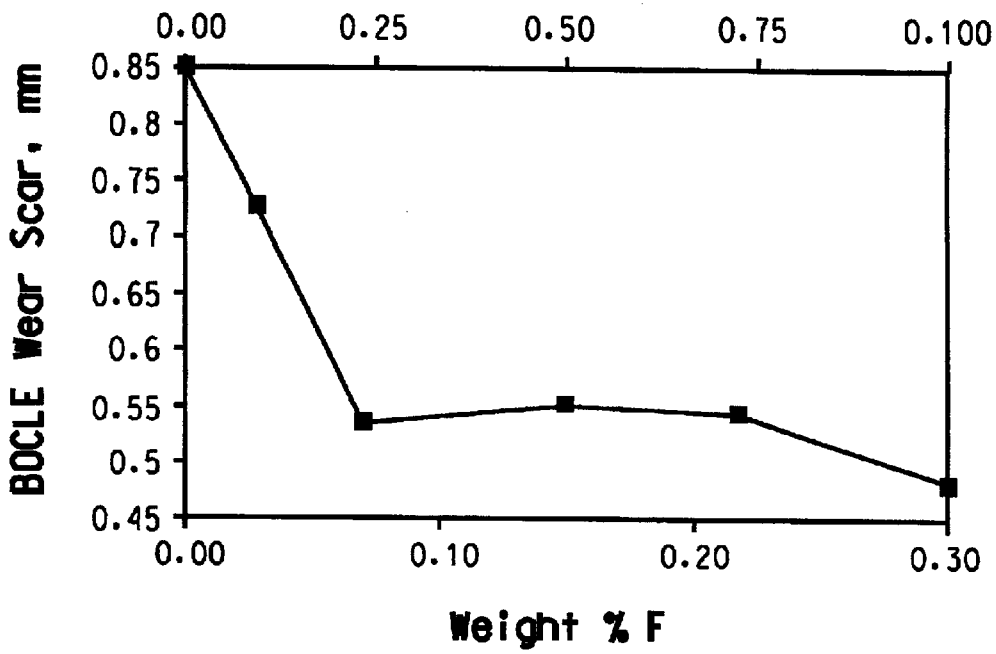
FIG. 3 shows BOCLE wear performance as a function of the weight percent of additive in 150N oil and as a function of the weight percent fluorine in the mixture of oil and additive the for the diester of Example 2 prepared from reaction of Dodecanedioic acid (DDDA), telomer alcohol and Exxal 13.

FIG. 3 shows the wear performance of this high-F-content material in 150N oil. The range of fluorine concentrations shown in FIG. 3 corresponds to weight concentrations of diester ranging up to 1%. Samples of 150N containing 0.25% diester (equivalent to 0.07%F) or more were hazy at ambient temperature, due to the limited solubility of the highly fluorinated diester component, $R_fO(O)C-(CH_2)_x-C(O)OR_f$, but were homogeneous at the 80° C. BOCLE test temperature. The response is very non-linear. A very strong anti-wear effect is obtained with only very small concentrations of the additive. The properties of the mixture of 150N oil and additive are much better than the properties expected based on simple linear effects and overall composition. The anti-wear performance achieved in FIG. 3, through use of the non-symmetrical, partially fluorinated diesters of the present invention, without other additives, is comparable to that of fully formulated motor oil.

EXAMPLE 3

The following Example describes the condensation esterification of DDDA using methanesulfonic acid catalyst and the preparation of DDDA diester using a mixture of 50 mole % Telomer alcohol-L and 50 mole % Exxal 13.

A 500 mL round bottom flask was charged with 69.06 g DDDA (MW 230.3, 0.3 mole), 130.41 g Telomer alcohol-L (average molecular weight≈414, 0.315 mole), 62.37 g Exxal 13 tridecyl alcohol from Exxon (FW≈198, 0.315 mole), 0.29 g methanesulfonic acid (MW 96.1, 0.003 mole), and 100 g mixed xylenes. The reaction flask was fitted with an 8" Vigreux column topped with a Dean-Stark trap and condenser. The reaction was heated to reflux to drive off water, which was separated in the Dean-Stark trap, xylene overflow being returned to the reaction flask. The reaction was followed by water removal and by periodic sampling and titration for acid number.

After 10 and ½ hours reaction time, the acid number had decreased to 1.6 mg KOH/g, and the reaction was considered to be complete.

The reaction product was brown. The reaction product was washed, at 70–80° C., with 330 g of 0.2% aqueous sodium hydroxide. Phases were inverted, with a brown aqueous phase on top and the denser ester phase on the bottom. The lower ester phase was very cloudy. After separating the caustic wash, the ester phase was washed three times with 300 mL portions of warm water. The acid number was 0.56 mg KOH/g.

The crude ester was sparged with nitrogen and heated from room temperature to a temperature of 210–220° C. over a period of 90 minutes to remove xylene, water, and other low boilers.

The yield was 215.72 g of a waxy tan solid having an acid number 0.75 mg KOH/g.

The same basic procedure as above was used to prepare other partially fluorinated esters, listed in Table 5. In all cases, the non-fluorinated alcohol was Exxal 13, tridecyl alcohol from Exxon. Due to difficulty obtaining reliable F elemental analysis, ester end groups were also analyzed by $^1$H NMR. The chemical shift region between 3.5 and 4.5 ppm downfield of tetramethylsilane reveals the $CH_2$ protons attached to the ester oxygen. In the case of $R_f$, these $CH_2$ protons are cleanly separated and downfield from the $CH_2$ protons of $R_h$. The relative molar amounts of $R_f$ and $R_h$ can be calculated from the integrals of these two groups. Where elemental analysis and NMR disagree, the NMR method is believed to be more reliable. Table 5. Partially fluorinated esters prepared by condensation esterification using methanesulfonic acid catalyst

| Preparation | Diacid | Partially Fluorinated alcohol | Mole fraction partially fluorinated alcohol | Acid number (mg KOH/g) | Wt % F (elemental analysis) | Wt % F (by NMR) |
|---|---|---|---|---|---|---|
| 9 | Adipic | Telomer alcohol-L | 0.025 | 0.34 | 1.92 | 2.6 |
| 10 | Adipic | Telomer alcohol | 0.025 | 0.29 | 2.25 | 3.2 |
| 11 | Azelaic | Telomer Alcohol-L | 0.025 | 0 | 1.83 | 1.66 |
| 12 | C14 diacid | Telomer alcohol-L | 0.025 | 0.27 | 1.39 | 1.28 |
| 13 | Corfree M1 | Telomer alcohol-L | 0.025 | 0 | 1.23 | 1.39 |
| 14 | Corfree M1 | Telomer alcohol-L | 0.025 | 0.6 | 1.32 | 1.49 |
| 15 | DDDA | Poly HEPO alcohol | 0.025 | 0.1 | 4.17 | |
| 16 | DDDA | Telomer alcohol | 0.025 | | | |
| 17 | DDDA | Telomer alcohol | 0.025 | 0.55 | 2.1 | 2.4 |
| 18 | DDDA | Telomer alcohol | 0.025 | 0.13 | 1.86 | 2 |

-continued

| Preparation | Diacid | Partially Fluorinated alcohol | Mole fraction partially fluorinated alcohol | Acid number (mg KOH/g) | Wt % F (elemental analysis) | Wt % F (by NMR) |
|---|---|---|---|---|---|---|
| 19 | DDDA | Telomer alcohol | 0.023 | 0.1 | 0 | 0 |
| 20 | DDDA | Telomer alcohol | 0.024 | 0 | 0 | 0 |
| 21 | DDDA | Telomer alcohol-L | 0.025 | 0.18 | 1.87 | 2.1 |
| 22 | DDDA | Telomer alcohol-L | 0.125 | 0.24 | 3.01 | 9.47 |
| 23 | DDDA | Telomer alcohol-L | 0.05 | 0.2 | | 4.06 |
| 24 | DDDA | Telomer alcohol-L | 0.025 | 0.18 | 1.82 | 1.92 |
| 25 | DDDA | Telomer alcohol-L | 0.25 | 0.3 | 16.68 | 17.3 |
| 26 | DDDA | Telomer alcohol-L | 0.5 | 0.751 | 34.6 | 34.3 |
| 27 | DDDA | Telomer ethoxylate alcohol | 0.025 | 0.27 | 2.36 | 3.4 |
| 28 | Sebacic | Telomer alcohol-L | 0.025 | 0.2 | 1.58 | 1.63 |
| 29 | Suberic | Telomer alcohol-L | 0.025 | 0.26 | 0.72 | 1.91 |

Figure 4:
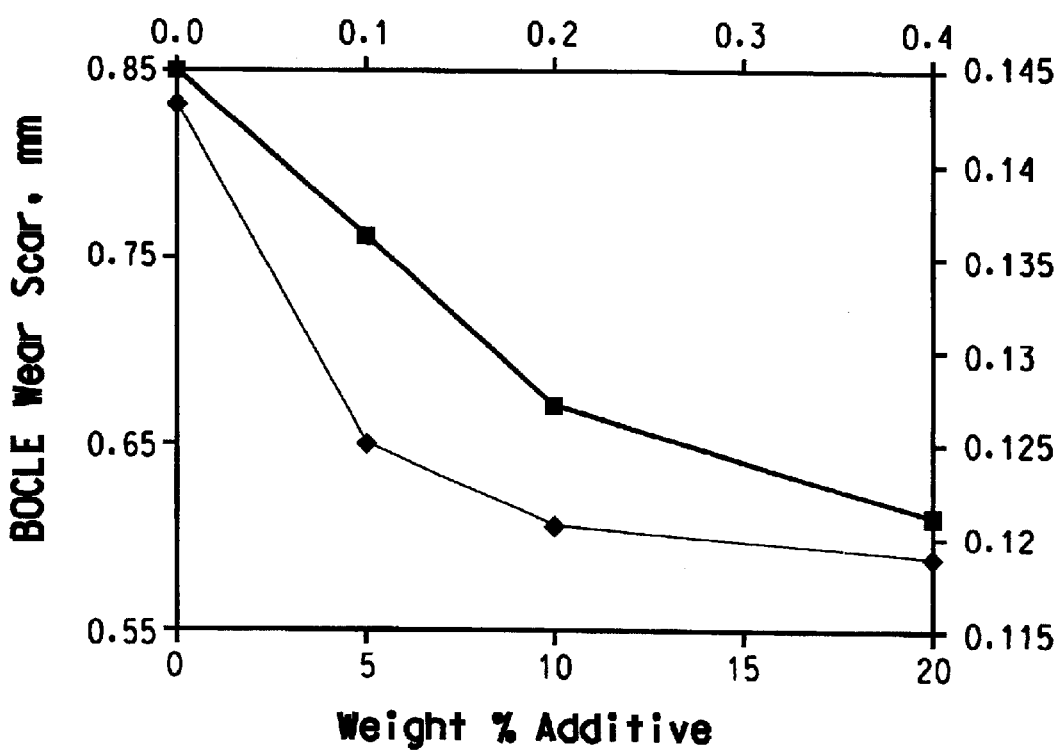
FIG. 4 shows wear performance of the diester additive of Example 3 as a function of the weight percent of additive in 150N oil and as a function of the weight percent fluorine in the mixture of oil and additive.
Figure 5:
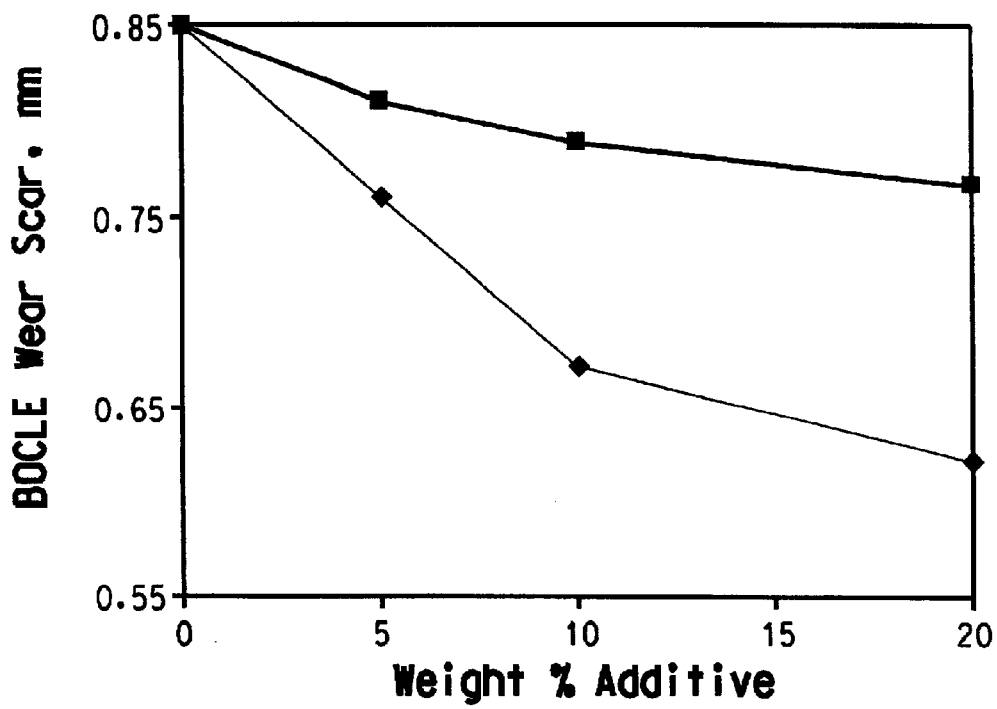
FIG. 5 shows a comparison of wear reduction of preparation 18, Example 3 to that of a commercially available non-fluorinated ester additive as a function of the weight percent of additive present in the additive/oil mixture.

FIG. 4 shows the wear and friction performance of a low-F-content material (≈2% F), sample 18 in Table 5, in 150N oil. This low-F-content material was completely soluble even at 20% by weight concentration (0.4 wt. percent F). FIG. 5 compares the anti-wear performance of this low-F material to a similar non-fluorinated diester, ditridecyl dodecanedioate (Hatcol 2907, from Hatco), showing the significant improvement in wear performance from only a very small amount of F incorporation.

Anti-wear and friction reducing performance of different chain length diesters from $C_6$ to $C_{14}$ was compared. All of these non-symmetric, partially fluorinated diesters imparted some benefits, with the longer chain diacids giving the greater benefits. Therefore, the preferred number of carbon atoms in the backbone is 9 or more or the wear scar by the BOCLE test as described herein is less than about 0.75 when the additive is present at about 0.2% fluorine.

EXAMPLE 4

The following Example describes the transesterification of dimethyl dodecanedioate using p-toluenesulfonic acid catalyst and the preparation of DDDA diester using a mixture of 50 mole % Exxal 13 and 50 mole % 1H, 1H, 5H-octafluoro-1-pentanol.

A mixture of 51.68 g dimethyl dodecanedioate (0.2 mole), 41.58 g Exxal 13 (0.21 mole), 48.73 g 1H, 1H, 5H-octafluoro-1-pentanol (0.21 mole), and 0.38 g p-toluenesulfonic acid was heated, and methanol distilled off. When the reaction temperature reached 198° C., GC analysis showed the dimethyl dodecanedioate to be essentially gone, indicating that the reaction had gone nearly to completion. After cooling, the product was washed with brine, 1% aqueous NaOH, and water, then treated with basic alumina and filtered. The final acid number was ≦0.1 mg KOH/g.

The same basic procedure was used to prepare other diesters, listed in Table 6. The non-fluorinated alcohol was Exxal 13 in all cases.

TABLE 6

DDDA diesters prepared according to Example 4.

| Preparation | Partially Fluorinated alcohol | Mole fraction partially fluorinated alcohol | Acid number (mg KOH/g) | Wt % F (elemental analysis) | Wt % F (by NMR) |
|---|---|---|---|---|---|
| 30 | Telomer alcohol-L | 0.025 | | 1.12 | 1.24 |
| 31 | 1H, 1H, 5H-octafluoro-1-pentanol | 0.5 | 0.1 | | |
| 32 | 1H, 1H, 2H, 2H-perfluoro-1-octanol | 0.5 | 0.1 | | |
| 33 | 1H, 1H heptafluoro-1-butanol | 0.5 | 0.1 | | |
| 34 | 1H, 1H-perfluoro-1-octanol | 0.5 | 0.1 | | |
| 35 | Telomer alcohol | 0.025 | 2 | | |
| 36 | Telomer alcohol | 0.025 | 0.52 | 1.45 | 1.63 |

Comparative Example 1

The following comparative Example describes the preparation of di(telomer alcohol)2-methylglutarate by one-step esterification of 2-methylglutaronitrile (MGN).

A mixture of 32.44 g MGN (0.3 mole), 18.05 g water (1 mole), and 304.2 g Telomer alcohol (0.67 mole) was preheated to 60° C., then 60.0 g sulfuric acid (0.61 mole) was added cautiously. The $H_2SO_4$ was added over ≈30 minutes to maintain reflux. After the acid was added, the reaction was refluxed for an additional 3 hours. The crude ester was decanted from the ammonium bisulfate salt phase while warm, then washed with 5% aqueous sodium bicarbonate.

The product was dried by heating to ≈100° C. under reduced pressure (≈0.1 kPa). The product was a tan, waxy solid with a wide melting range (≈45–70° C.). Solubility in 150N oil was found to be only ≦0.1% at ambient temperature.

EXAMPLE 5
This Example describes the esterification of 2-methylglutaronitrile (MGN) in a Two-step Reaction:

A mixture of 43.26 g MGN (0.4 mole) and 36.0 g water (2 mole) was preheated to 85° C. Sulfuric acid (80.42 g, 0.82 mole) was added via dropping funnel, at a rate adjusted to maintain reaction temperature at 115–135° C. Following the addition, the reaction was held at temperature for 1 hour, then cooled to 100° C. A mixture of 9.49 g Telomer alcohol (0.021 mole) and 162.16 g Exxal 13 (0.819 mole) was added over 7 minutes, then the reaction was heated and held in the range 127–135 for 1 hour. After cooling, the crude ester was decanted from ammonium bisulfate salts. The crude ester was mixed with 100 g mixed xylenes and 0.38 g methanesulfonic acid, placed in a reactor fitted with a Vigreux column and Dean-Stark trap, and heated to reflux to drive off water to complete the esterification. The reaction was sampled periodically and acid number determined. When the acid number had leveled off, indicating that no further reaction was occurring, the heat was turned off. The product was washed with an equal volume of 0.5% NaOH solution, then 5 times with water. Warming the mixture to 60° C. during the water washes improved phase separation. The washed ester was sparged with nitrogen while being heated to 200° C. to drive off water. The final acid number was 0.15 mg KOH/g.

2-Methylglutarate diesters prepared according to Comparative example 1 and example 5 are summarized below in Table 7. In all cases, the non-fluorinated alcohol was Exxal 13.

hydrogen-bonding solvents such as mineral oils The alcohols used in this series of reactions were tridecyl alcohol (Exxal 13 from Exxon) and the partially-fluorinated alcohol, Zonyl BA (from Dupont). Several amines were used, including Armeen 2HT, Armeen HTMD, and Armeen 18D (from Akzo Nobel Chemicals) and Adogen 101, and Adogen 140 (from Sherex/Witco). These amines are described in table 8 below.

TABLE 8

| Amine (CAS number) | Description (type of amine, formula estimated from $^1$H NMR) |
|---|---|
| Armeen 2HT (61789-79-5) | Di (hydrogenated tallowalkyl)amine ($R_2NH$, average R = $C_{17.6}H_{36.2}$) |
| Armeen HTMD (61788-45-2) | Hydrogenated tallowalkylamine ($RNH_2$, average R = $C_{17.5}H_{36}$) |
| Armeen 18D (124-30-1) | Octadecyl amine ($RNH_2$, R = $C_{18}H_{37}$) |
| Adogen 101 (68037-92-3) | $C_{16}$–$C_{22}$ amine ($RNH_2$, average R = $C_{20.3}H_{41.6}$) |
| Adogen 140 (68037-91-2) | Hydrogenated tallowalkylamine, also indicated to be $C_{14}$ to $C_{18}$ amine ($RNH_2$, average R = $C_{18.1}H_{37.2}$) |

Each reaction employed 1 mmol of DDDA, but the amounts of the other reactants were systematically varied as follows. The mole ratio of Exxal 13/DDDA was varied between 0 and 1.34, the mole ratio of Zonyl BA/DDDA was varied between 0 and 1, and the mole ratio of amine/DDDA was varied between 0.33 and 2.0, under the constraint that the mole ratio of the total amount of alcohol and amine together was restricted to the theoretically-required 2.0 moles per mole DDDA.

More specifically, for the case where the amine tested was Armeen 2HT, the following eight reaction mixtures in table 9 were prepared, where the numbers represent the amount of

TABLE 7

| Preparation | Preparation method | Partially fluorinated alcohol | Mole fraction partially fluorinated alcohol | Acid number (mg KOH/g) | Wt % F (elemental analysis) | Wt % F (by NMR) |
|---|---|---|---|---|---|---|
| 37 | 5 | Telomer alcohol | 0.025 | 0.15 | 1.98 | 2.06 |
| 38 | 5 | Telomer alcohol-L | 0.025 | 0.19 | 1.13 | 1.2 |
| 39 | Comparative example 1 | Telomer alcohol | 0.5 | 0.07 | | |
| 40 | Comparative example 1 | Telomer alcohol | 1 | | | |
| 41 | 5 | Telomer alcohol-L | 0.05 | 2.4 | 1.16 | 2.9 |
| 42 | 5 | Telomer alcohol-L | 0.125 | 0.3 | 5.33 | 8.56 |

The following examples 6 and 7 show that partially-fluorinated amide-esters can be prepared which have solubility in conventional mineral oil and that these partially fluorinated amide-esters can be used as lubricant additives to reduce friction and wear.

EXAMPLE 6
Preparation and Solubility of Partially-Fluorinated Amide-Esters from Dodecanedioic Acid, Tridecyl Alcohol, and Zonyl BA Partially-Fluorinated Alcohol:

A set of screening experiments was conducted to prepare partially-fluorinated amide-esters from dodecanedioic acid (DDDA) for assessing their solubility in non-polar, noneach ingredient used, in mmol (except for the methanesulfonic acid esterification catalyst, which was used in 10 µl quantity in each mixture).

TABLE 9

| Ingredient | Rx #1 | Rx #2 | Rx #3 | Rx #4 | Rx #5 | Rx #6 | Rx #7 | Rx #8 |
|---|---|---|---|---|---|---|---|---|
| DDDA | 1.0 | 1.0 | 1.0 | 1.0 | 1.0 | 1.0 | 1.0 | 1.0 |
| Exxal 13 | 0.66 | | | 1.34 | 0.67 | | 0.5 | 1.34 |
| Zonyl BA | | | 0.66 | 0.33 | 0.66 | 1.0 | 1.0 | |

TABLE 9-continued

| Ingredient | Rx #1 | Rx #2 | Rx #3 | Rx #4 | Rx #5 | Rx #6 | Rx #7 | Rx #8 |
|---|---|---|---|---|---|---|---|---|
| Armeen 2HT | 1.34 | 1.34 | 0.33 | 0.67 | 1.0 | 0.5 | 0.66 | 2.0 |
| Methanesulfonic acid (catalyst) | 10 μl | 10 μl | 10 μl | 10 μl | 10 μl | 10 μl | 10 μl | 10 μl |

A similar set of eight reactions was prepared for each of the five amines tested, for a total of 40 reaction mixtures.

The reaction mixtures were prepared in 2 mL glass vials. Reactions were conducted by placing the open-topped vials in a heated block maintained at 150° C. and maintaining that temperature for at least 18 hours (generally 18–24 hours). This was intended to allow escape of water formed from the esterification and amidation reactions. The crude reaction products were used without purification for solubility testing.

Relative solubility of the products from these reactions was assessed by mixing the reaction product with 30 ml tetrahydrofuran (THF), then collecting and weighing any undissolved material on a 0.2 μm Teflon®-coated fiberglass membrane filter. The products from Armeen HTMD and Adogen 140, both hydrogenated tallowalkylamine, were judged to be very similar, so the Armeen reactions were not filtered. Residue weights are given in the table 10 below.

TABLE 10

| Amine | Rx #1 | Rx #2 | Rx #3 | Rx #4 | Rx #5 | Rx #6 | Rx #7 | Rx #8 |
|---|---|---|---|---|---|---|---|---|
| Armeen 2HT | 0.05 | 0.18 | 0 | 0 | 0.05 | 0.02 | 0 | 0.56 |
| Armeen 18D | 0.43 | 0.37 | 0.06 | 0.15 | 0.24 | 0.12 | 0.14 | 0.48 (Note 1) |
| Adogen 101 | 0.61 | 0.46 | 0.05 | 0.13 | 0.34 | 0.08 | 0.04 | 0.91 |
| Adogen 140 | 0.35 | 0.85 | 0.04 | 0.16 | 0.17 | 0.07 | 0.07 | 0.97 |
| Average of Armeen 18D, Adogen 101, and Adogen 140 | 0.46 | 0.56 | 0.05 | 0.15 | 0.25 | 0.09 | 0.08 | 0.79 |

(Note 1-This was the first filtration performed, and inadvertently employed a polycarbonate filter membrane, which was incompatible with the THF solvent. The filter membrane was partially dissolved and some of the insoluble material was lost, so the 0.48 g represents the minimum quantity of undissolved solid present in the original THF mixture.)

By examining the results in the table, it is clear that the amides prepared from the primary amines Armeen 18D, Adogen 101, and Adogen 140 have similar solubility properties while the amides prepared from the secondary amine Armeen 2HT have significantly higher solubility (less insoluble residue). It is possible to prepare amide-esters with significant amounts of fluorinated ester groups which still have good solubility, particularly using the secondary amine Armeen 2HT (reactions 5 and 6). The mole ratio of reaction 3 provided products, which were almost completely soluble, even in the case of the primary amines. It is also clear that the diamides have lower solubility (reaction 8 results).

Figure 6:
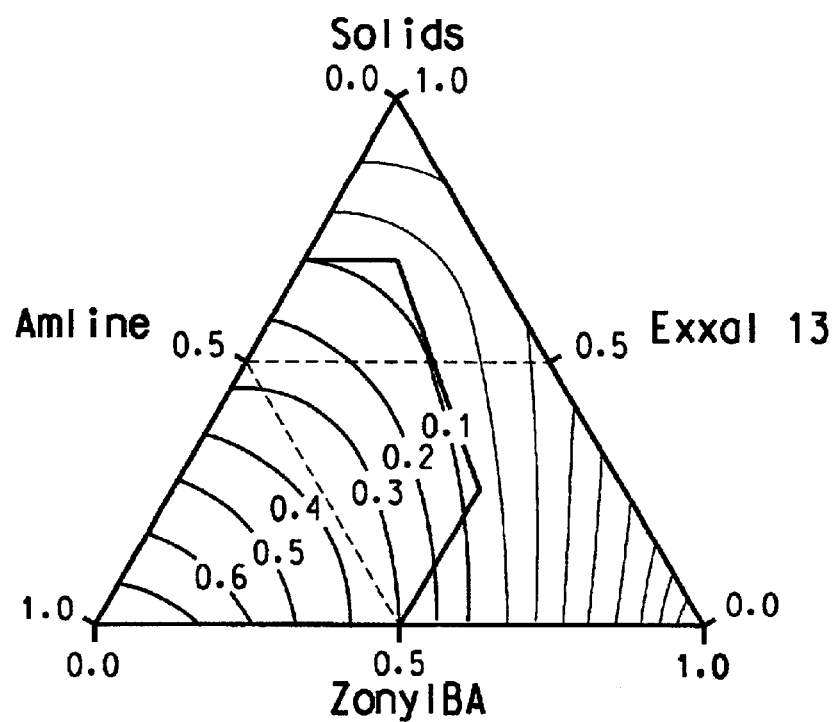
FIG. 6 illustrates a triangular plot showing how the amount of insoluble solids (i.e., residue) varies with the composition of the mixed amide-esters derived from primary amines of Example 6.
Figure 7:
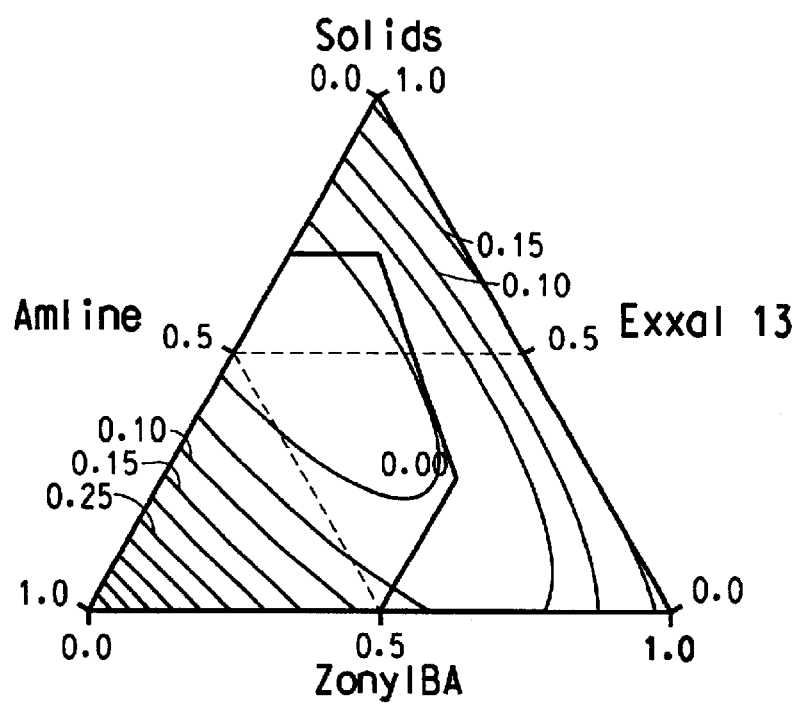
FIG. 7 illustrates a triangular plot showing how the amount of insoluble solids (i.e., residue) varies with the composition of the mixed amide-esters derived from secondary amines of Example 6.

To help visualize and interpret these results, the solubility data was evaluated using an experimental design software package, ECHIP (ECHIP, Inc., 724 Yorklyn Road, Hockessin, Del., 19707). The model used was an interaction model, which considers dependence on individual components (e.g. amine content) as well as interactions (e.g. cross terms such as amine×Exxal 13). FIGS. 6 and 7 illustrate the ECHIP model results showing how the amount of insoluble solid varies with on the composition of the amide-ester. In the figures, end group composition is normalized to 1.0; for example, the ester amide with equal amounts of Zonyl, Exxal, and amide end groups would lie at the center of the triangle (0.33 mole fraction of each end group).

From these triangle plots, several conclusions can be drawn: (1) It is possible to prepare partially-fluorinated mixed ester amides which have good solubility in THF, (2) the amount of amine present in the composition (resulting in amide ends) has a major effect on solubility, with the least amount of insoluble solid being present at the lowest amide content, (3) compositions in the center region of the three-component composition space have highest solubility in THF.

Since the mole ratio of reaction 3 provided products which were almost completely soluble, even in the case of the primary amines, this reactant ratio was chosen for scaleup. One example is given below.

EXAMPLE 7

Preparation of Ester Amide from Dodecanedioic Acid, Zonyl BA, Tridecyl Alcohol, and Di(Hydrogenated Tallowalkyl)Amine:

A mixture of 46.06 g DDDA (0.200 mole), 60.98 g tridecyl alcohol (Exxal 13 from Exxon, 0.308 mole), 31.68 g Zonyl BA (0.066 mole), 33.67 g Armeen 2HT (0.066 mole), 10 g Dowex 50W X2-400 strong acid ion exchange resin (used as esterification-amidation catalyst), and 63.84 g cyclohexane was heated to reflux. The mole ratio of the reactants used, DDDA:Exxal:Zonyl:Armeen was 1.0:1.54:0.33:0.33, is similar to screening reaction #3 above example 6, except that the amount of Exxal was increased to ensure complete reaction and to increase reaction rate. Water was separated from refluxing cyclohexane using a condenser and Dean-Stark trap. The reaction temperature was initially about 100–105° C. Water was drained from the trap and cyclohexane was added as necessary to maintain reaction temperature at or below 118° C. After 25 hours total reaction time, the acid number was 58. The reaction was filtered to remove the Dowex catalyst. The filtered crude product was heated to 200° C. while sparging with nitrogen, then the pressure was reduced to 50 torr while continuing the nitrogen sparge. The purpose of this stripping procedure was to continue the reaction and to remove excess, unreacted Exxal 13. The stripping procedure was continued for about 7 hours, when analysis by gas chromatography showed that residual Exxal 13 had been removed. The acid number had decreased to 19.

The product was analyzed by $^1$H NMR, which was interpreted as follows. A triplet at 4.4 ppm was assigned to the O—CH$_2$— protons of a Zonyl ester end. A group of broad mulitplets between about 3.8 and 4.2 ppm was assigned to the O—CH$_2$— protons of Exxal ester ends (many different structures because Exxal 13 is a complex mixture). A pair of mulitplets centered around 3.25 ppm was assigned to the —N—CH$_2$— protons of an amide end derived from the Armeen 2HT. Integration of these signals suggested a composition of about 5.2% Zonyl ends, 80.7% Exxal ends, and 14.2% Armeen amide ends (composition normalized to 100%), which suggested a fluorine content from the Zonly ends of 4.8% F. Elemental analysis showed 4.96%F.

Figure 8:
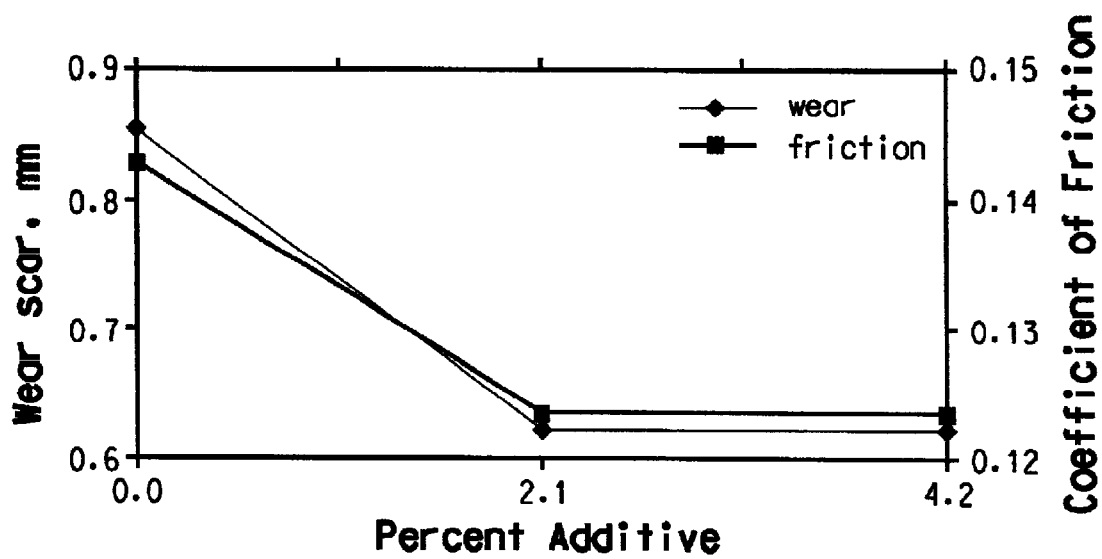
FIG. 8 shows wear performance of the diester additive of Example 7 as a function of the weight percent of additive in 150N oil and as a function of the parts per million of fluorine in the mixture of oil and additive.

This material was tested using the BOCLE procedure described previously. Results are shown in FIG. 8.

Having thus described and exemplified the invention with a certain degree of particularity, it should be appreciated that the following claims are not to be so limited but are to be afforded a scope commensurate with the wording of each element of the claim and equivalents thereof.

I claim:

1. A non-symmetric, partially fluorinated compound having a molecular structure:

$$R_{1f}-F'-R_2-F''-R_{3h}$$

wherein $R_{1f}$ represents a wholly or partially fluorinated $C_1$ to $C_{40}$ organic residue end group other than a fluoroalkylether group; F' and F'' represent functional linkages which are carboxylic esters; $R_2$ represents the hydrocarbon backbone selected from the group consisting of a $C_7$ to $C_{30}$ alkyl, $C_3$ to $C_{30}$ cycloalkyl, an aromatic group, and mixtures thereof; provided when $R_2$ is an aromatic group, then the fluorinated compound is difunctional, and $R_{3h}$ represents a non-fluorinated $C_1$ to $C_{40}$ organic residue end group.

* * * * *